United States Patent [19]

Warren et al.

[11] Patent Number: 5,643,791
[45] Date of Patent: Jul. 1, 1997

[54] **CHARACTERIZATION AND STRUCTURE OF AN ENDODGLUCANASE GENE OF *CELLULOMONAS FIMI***

[75] Inventors: R. Anthony J. Warren; Douglas G. Kilburn, both of Vancouver; Robert C. Miller, Jr., North Vancouver, all of Canada

[73] Assignee: University of British Columbia, Vancouver, Canada

[21] Appl. No.: 185,303

[22] Filed: Jan. 19, 1994

Related U.S. Application Data

[63] Continuation of Ser. No. 902,460, Jun. 19, 1992, abandoned, which is a continuation of Ser. No. 630,396, Dec. 18, 1990, abandoned, which is a continuation of Ser. No. 894,326, Aug. 7, 1986, abandoned.

[51] Int. Cl.$^6$ .............................. C12N 1/21; C12N 15/52; C12N 15/63
[52] U.S. Cl. .............................. 435/252.33; 435/252.3; 435/320; 536/23.2
[58] Field of Search .................. 435/209, 252.3; 935/72; 536/23.2, 252.3, 252.33, 320.1, 203

[56] References Cited

U.S. PATENT DOCUMENTS

| | | | |
|---|---|---|---|
| 4,666,828 | 5/1987 | Gusella | 436/6 |
| 4,703,008 | 10/1987 | Lin | 435/240.2 |

OTHER PUBLICATIONS

Beguin et al., "Sequence of a Cellulase Gene of the Thermophilic Bacterium *Clostridium thermocellum*", *Journal of Bacteriology*, 162:(1):102–105 (Apr. 1985).

Bibb et al., "The Relationship Between Base Composition and Condon Usage in Bacterial Genes and It use for the Simple and Reliable Identification of Protein–Coating Sequences", *Gene*, 30:157–166 (1984).

Chamblis et al., "Baterial in vitro Protein–Synthesizing Systems", *Methods in Enzymology*, 101:[37]:598–605 (1983).

Collmer and Wilson, "Cloning and Expression of a Thermomonospora YX Endocellulase Gene in *E. coli*", *Bio/Technology*, pp. 594–601 (Sep. 1983).

Cornet et al., "Characterization of Two Cel (Cellulose Degradation) Genes of *Clostridium thermocellum* Coding for Endoglucanases", pp. 589–594 (Sep. 1983).

Curry et al., "Expression and Secretion of a *Cellulomonas fimi* Exoglucanase in *Saccharomyces cerevisiae*", *Applied and Environmental Microbiology*, 54:(2):476–484 (1988).

Gilkes et al., "Isolation and Characterization of *Escherichia coli* Clones Expressing Cellulase Genes from *Cellulomonas fimi*", *J. Gen. Microbial.* 130:1377–1384 (1984).

Gilkes et al., "Mode of Action and Substrate Specificities of Cellulases from Cloned Baterial Genes", *J. Biol. Chem.*, 259:(16):10455–10459 (1984).

Gilkes et al., "A Mutant of *Escherichia coli* that Leaks Cellulase Activity Encoded by Cloned Cellulase Genes from *Cellulomonas fimi*", *Bio/Technology*, pp. 259–263 (Mar. 1984).

Gilkes et al., "Precise Excision of the Cellulose Binding Domains from Two *Cellulomonas fimi* Cellulases by a Homologous Protease and the Effect on Catalysis", *J. Biol. Chem.*, 263:(21):10401–10407 (1988).

Gilkes et al., "Domains in Microbial β–1,4–Glucanases; Sequence Conversation, Function, and Enzyme Families", *Microbiological Reviews*, 55:(2):303–315 (Jun. 1991).

Guo and Wu, "Exonuclease III: Use for DNA Sequence Analysis and in Specific Deletions of Nucleotides," *Methods in Enzymology*, 100:60–96 (1983).

Hinchliffe and Box, "Expression of the Cloned Endo–1,3–1, 4–β–glucanase Gene of *Bacillus subtilis* in *Saccharomyces cerevisiae*", *Current Genetics*, 8:471–475 (1984).

Inouye and Halegoua, "Secretion and Membrane Localization of Proteins in *Escherichia coli*", *CRC Critical Reviews in Biochemistry*, 7:339–371 (1980).

Kilburne et al., "Characterization of the Cellulases of *Cellulomonas fimi* and cloning of their Structural Genes in *Escherichia coli*", *Abstr.Pap.Am.Chem.Soc.* 189 Meet., Cell 55 (1985); provided as: *Derwent Biotechnology Abstracts*, 4:(2):85–12334 (1985).

Kotoujansky et al., "Molecular Cloning of *Erwinia chrysanthemi* Pectinase and Cellulase Structural Genes," *The EMBO Journal*, 4:(3):781–785 (1985).

Kreil, "Transfer of Proteins Across Membranes", *Ann. Rev. Biochem.*, 50:317–48 (1981).

Lansford et al., "The Cellulase System of *Cellulomonas fimi*", *Journal of General Microbiology*, 130:11367–1376 (1984).

Lansford et al., "Glycosylation of Bacterial Cellulases Prevents Proteolytic Cleavage Between Functional Domains", *FEBS Letters*, 225:(1, 2):163–167 (1987).

Maniatis et al., "Enzmes Used in Molecular Cloning", *Molecular Cloning, A Laboratory Manual*, pp. 100–101 (1982).

Messing, "New M13 Vectors for Cloning", *Methods in Enzymology*, 101:20–78 (1983).

Miller et al., "Measurement of Carboxymethylcellulae Activity", *Analytical Biochemistry*, 2:127–132 (1960).

(List continued on next page.)

*Primary Examiner*—Mindy Fleisher
*Assistant Examiner*—David Schmickel
*Attorney, Agent, or Firm*—Barbara Rae-Venter

[57] ABSTRACT

A biologically pure DNA sequence which encodes an endo 1,4-β-glucanase, useful for the efficient conversion of cellulose to glucose, is disclosed. Also disclosed are recombinant DNA cloning vehicles (vectors) that contain nucleotide sequences that encode for the aforesaid endoglucanase, proteins that exhibit endoglucanase activity, expression-controlling DNA sequences, microorganisms that contain recombinant DNA cloning vehicles, as well as messenger RNA sequences complementary to a DNA strand of the aforesaid DNA nucleotide sequences.

28 Claims, 10 Drawing Sheets

OTHER PUBLICATIONS

Millet et al., "Cloning of Ten Distinct DNA Fragments of *Clostridium thermocellum* Coding for Cellulases", *FEMS Letters*, 29:145–149 (1985).

Moser et al., "Purification and Characterization of Endoglucanase C of *Cellulomona fimi*, Cloning of the Gene, and Analysis of In Vivo Transcripts of the Gene", *Applied and Environmental Microbiology*, 55:(10):2480–2487 (Oct. 1989).

Murphy et al., "The DNA Sequence of the Gene and Genetic Control Sites for the Excreted *B. subtilis* Enzyme", *Nucleic Acids Research*, 12:(13):5355–5367 (1984).

Ohmura et al., "Length and Structural Effect of Signal Peptides Derived from *Bacillus subtilis* α-amylase on secretion of *Escherichia coli* β-lactamase in *B. subtilis* cells", *Nucleic Acids Research*, 12:(13):5307–5318 (1984).

O'Neill et al., "Structural of the Gene Encoding the Exoglucanase of *Cellulomonas fimi*", *Gene*, 44:325–330 (1986).

Owolabi et al., "Expression in *Escherichia coli* of *Cellulomonas fimi* Structural Gene for Endoglucanase B", *Applied and Environmental Microbiology*, 54:(2):518–523 (1988).

Sancar et al., "Simple Method for Identification of Plasmid-Coded Proteins", *Journal of Bacteriology*, 137:(1):692–693 (1979).

Shoemaker et al., "Molecular Cloning of Exo-Cellobiohydrolase I Derived from *Trichoderma reesei* strain L27", *Bio/Technology*, pp. 691–696 (Oct. 1983).

Skipper et al., "Secretion of a Bacterial Cellulase by Yeast", *Science*, 230:958–960 (1985).

Stuber and Bujard, "Organization of Transcriptional Signals in Plasmids pBR322 and pACYC184", *Proc. Natl. Acad. Sci. USA*, 78:(1):167–171 (1981).

Sutcliffe, "Complete Nucleotide Sequence of the *Escherichia coli* Plasmid pBR322", *Symp. Quant. Biol.* 43:77–90 (1979).

Teather and Wood, "Use of Congo Red–Polysaccharide Interactions in Enumeration and Characterization of Cellulolytic Bacteria from the Bovine Rumen", *Appl. Environ. Microbiol.*, 43:(4):777–780 (1982).

Teeri et al., "The Molecular Cloning of the Major Cellulase Gene From *Trichoderma reesei*", *Bio/Technology* (reprint) Oct. 1983.

Vieira and Messing, "The pUC Plasmids, and M13mp7–derived system for insertion mutagenesis and Sequencing with Synthetic Universal Primers", *Gene*, 19:259–268 (1982).

Watson, "Compilation of Published Signal Sequences", *Nucleic Acids Research*, 12:(13):5145–5164 (1984).

Wickner and Lodish, "Multiple Mechanisms of Protein Insertion Into and Across Membranes", *Science*, 230:400–407 (Oct. 1985).

Wong et al., "Characterization and Structure of an Endoglucanase Gene *cen A* of *Cellulomonas fimi*", *Gene*, 44:315–324 (1986).

Maniatis et al. In *Molecular Cloning, A Laboratory Manual*, Cold Spring Harbor, 1982, p. 143.

5' - - - - - - - - - - - -GGATCCGGACGGTGGGCGTCGTGGCCGACACC
                                    -516                    -496

GACGCGCTGGAGACGACCTTCGCGGACGTCGCGGACCTCGCGCGGCAGTGCCGG
                              -457

TTCGGCGACTGCCGGCACGAGCGGGAGCCGGGTGCGCGGTGCGGGCGGCCGTCGA
   -437                -417                -397

GTCGGGCGACCTGCCGGCCCGGCGGCTGGACTCGTGGCGGCGCCTGGAGCGCGAG
      -377                                         -338

GCGGCCTACCAGGCACGGCGCAGCGACGGCGGCTGGCCGCGGAGGAGCGCGCACG
           -318              -298                 -278

CTGGAAGAAGATCACCAAGGAGTACCAGCGGGGATGCGCGGGCCGGGGCGTCCG
                 -258

CGGAGCTGACGGGCCCGGGAGGCCCGCAGCCGGGCGGTGGGGAGTCCGCTCGGCG
-219                 -199               -179

CCAGCGGGTGTCGAAGCGACGGGTCGAAGCGCGCCAACGTCGCCCGATCCGGAAC
   -159              -139

TGAAGCGATTAGGAAATCCTCATCCGCTCGCGCCGTGGGGCATTCGTCGGGTTTC
       -100               -80                     -60

CTCGTCGGGACCCGCACGAGCGTGCCACGAGGCCCGAACCCAGGGAGCTCCTTG
          -40                -20

FIGURE 5A

```
Met Ser Thr Arg Arg Thr Ala Ala Ala Leu Leu Ala Ala Ala Ala
ATG TCC ACC CGC AGA ACC GCC GCA GCG CTG CTG GCG GCC GCG GCC
                15              30              45

Val Ala Val Gly Gly Leu Thr Ala Leu Thr Thr Thr Ala Ala Gln
GTC GCC GTC GGC GGT CTG ACC GCC CTC ACC ACC ACC GCC GCG CAG
                60              75              90
 ⇓
Ala Ala Pro Gly Cys Arg Val Asp Tyr Ala Val Thr Asn Gln Trp
GCC GCT CCC GGC TGC CGC GTC GAC TAC GCC GTC ACC AAC CAG TGG
                105             120             135

Pro Gly Gly Phe Gly Ala Asn Val Thr Ile Thr Asn Leu Gly Asp
CCC GGC GGC TTC GGC GCC AAC GTC ACG ATC ACC AAC CTC GGC GAC
                150             165             180

Pro Val Ser Ser Trp Lys Leu Asp Trp Thr Tyr Thr Ala Gly Gln
CCC GTC TCG TCG TGG AAG CTC GAC TGG ACC TAC ACC GCA GGC CAG
                195             210             225

Arg Ile Gln Gln Leu Trp Asn Gly Thr Ala Ser Thr Asn Gly Gly
CGG ATC CAG CAG CTG TGG AAC GGC ACC GCG TCG ACC AAC GGC GGC
   BamHI        240             255             270

Gln Val Ser Val Thr Ser Leu Pro Trp Asn Gly Ser Ile Pro Thr
CAG GTC TCC GTC ACC AGC CTG CCC TGG AAC GGC AGC ATC CCG ACC
                285             300             315

Gly Gly Thr Ala Ser Phe Gly Phe Asn Gly Ser Trp Ala Gly
GGC GGC ACG GCG TCG TTC GGG TTC AAC GGC TCG TGG GCC GGG
                330             345
```

FIGURE 5B

```
Ser  Asn  Pro  Thr  Pro  Ala  Ser  Phe  Ser  Leu  Asn
TCC  AAC  CCG  ACG  CCG  GCG  TCG  TTC  TCG  CTC  AAC
360                      375                       390

Gly  Thr  Thr  Cys  Thr  Gly  Thr  Val  Pro  Thr  Thr
GGC  ACC  ACC  TGC  ACG  GGC  ACC  GTG  CCG  ACG  ACC
                    405                      420

Ser  Pro  Thr  Pro  Thr  Pro  Thr  Pro  Thr  Thr  Pro
AGC  CCC  ACG  CCG  ACC  CCG  ACG  CCG  ACG  ACC  CCC
               435                      450

Thr  Pro  Thr  Pro  Thr  Pro  Thr  Pro  Thr  Pro  Thr
ACG  CCG  ACG  CCG  ACC  CCG  ACC  CCC  ACC  CCC  ACG
          465                      480

Pro  Thr  Val  Thr  Pro  Gln  Pro  Thr  Ser  Gly  Phe
CCG  ACG  GTC  ACG  CCG  CAG  CCG  ACC  AGC  GGC  TTC
     495                      510

Tyr  Val  Asp  Pro  Thr  Thr  Gln  Gly  Tyr  Arg  Ala
TAC  GTC  GAC  CCG  ACG  ACG  CAG  GGC  TAC  CGC  GCG
525                      540                       555

Trp  Gln  Ala  Ala  Ser  Gly  Thr  Asp  Lys  Ala  Leu
TGG  CAG  GCC  GCG  TCC  GGC  ACG  GAC  AAG  GCG  CTG
                    570                       585

Leu  Glu  Lys  Ile  Ala  Leu  Thr  Pro  Gln  Ala  Tyr
CTC  GAG  AAG  ATC  GCG  CTC  ACC  CCG  CAG  GCG  TAC
               600                      615

Trp  Val  Gly  Asn  Trp  Ala  Asp  Ala  Ser  His  Ala
TGG  GTC  GGC  AAC  TGG  GCC  GAC  GCG  TCG  CAC  GCG
          630                      645
```

FIGURE 5C

```
Gln Ala Glu Val Ala Asp Tyr Thr Gly Arg Ala
CAG GCC GAG GTC GCC GAC TAC ACC GGC CGC GCC
        660                 675

Val Ala Ala Gly Lys Thr Pro Met Leu Val Val
GTC GCG GCC GGG AAG ACG CCG ATG CTC GTC GTC
690                 705                 720

Tyr Ala Ile Pro Gly Arg Asp Cys Gly Ser His
TAC GCG ATC CCG GGC CGC GAC TGC GGC TCG CAC
                735                 750

Ser Gly Gly Gly Val Ser Glu Ser Glu Tyr Ala
TCC GGC GGT GGT GTG TCC GAG TCC GAG TAC GCG
            765                 780

Arg Trp Val Asp Thr Val Ala Gln Gly Ile Lys
CGC TGG GTC GAC ACC GTC GCG CAG GGC ATC AAG
        795                 810

Gly Asn Pro Ile Val Ile Leu Glu Pro Asp Ala
GGC AAC CCG ATC GTG ATC CTC GAG CCC GAC GCG
    825                 840

Leu Ala Gln Leu Gly Asp Cys Ser Gly Gln Gly
CTC GCG CAG CTC GGC GAC TGC TCC GGC CAG GGT
855                 870                 885

Asp Arg Val Gly Phe Leu Lys Tyr Ala Ala Lys
GAC CGC GTC GGC TTC CTC AAG TAC GCC GCC AAG
            900                 915
```

FIGURE 5D

| Ser | Leu | Thr | Leu | Lys | Gly | Ala | Arg | Val | Tyr | Ile |
|-----|-----|-----|-----|-----|-----|-----|-----|-----|-----|-----|
| TCG | CTC | ACC | CTC | AAG | GGC | GCG | CGC | GTC | TAC | ATC |
|     |     |     | 930 |     |     |     |     | 945 |     |     |

| Asp | Ala | Gly | His | Ala | Lys | Trp | Leu | Ser | Val | Asp |
|-----|-----|-----|-----|-----|-----|-----|-----|-----|-----|-----|
| GAC | GCG | GGC | CAC | GCG | AAG | TGG | CTG | TCG | GTC | GAC |
|     |     | 960 |     |     |     |     | 975 |     |     |     |

| Thr | Pro | Val | Asn | Arg | Leu | Asn | Gln | Val | Gly | Phe |
|-----|-----|-----|-----|-----|-----|-----|-----|-----|-----|-----|
| ACG | CCG | GTG | AAC | CGC | CTC | AAC | CAG | GTC | GGC | TTC |
|     | 990 |     |     |     | 1005 |   |     |     |     |     |

| Glu | Tyr | Ala | Val | Gly | Phe | Ala | Leu | Asn | Thr | Ser |
|-----|-----|-----|-----|-----|-----|-----|-----|-----|-----|-----|
| GAG | TAC | GCG | GTG | GGC | TTC | GCG | CTC | AAC | ACG | TCG |
| 1020 |    |     |     |     | 1035 |   |     |     |     | 1050 |

| Asn | Tyr | Gln | Thr | Thr | Ala | Asp | Ser | Lys | Ala | Tyr |
|-----|-----|-----|-----|-----|-----|-----|-----|-----|-----|-----|
| AAC | TAC | CAG | ACG | ACG | GCG | GAC | AGC | AAG | GCG | TAC |
|     |     |     |     | 1065 |    |     |     |     | 1080 |    |

| Gly | Gln | Gln | Ile | Ser | Gln | Arg | Leu | Gly | Gly | Lys |
|-----|-----|-----|-----|-----|-----|-----|-----|-----|-----|-----|
| GGC | CAG | CAG | ATC | TCG | CAG | CGG | CTG | GGC | GGC | AAG |
|     |     |     |     | 1095 |    |     |     | 1110 |    |     |

| Lys | Phe | Val | Ile | Asp | Thr | Ser | Arg | Asn | Gly | Asn |
|-----|-----|-----|-----|-----|-----|-----|-----|-----|-----|-----|
| AAG | TTC | GTC | ATC | GAC | ACC | TCG | CGC | AAC | GGC | AAC |
|     |     | 1125 |    |     |     |     | 1140 |    |     |     |

| Gly | Ser | Asn | Gly | Glu | Trp | Cys | Asn | Pro | Arg | Gly |
|-----|-----|-----|-----|-----|-----|-----|-----|-----|-----|-----|
| GGC | TCG | AAC | GGC | GAG | TGG | TGC | AAC | CCG | CGC | GGC |
| 1155 |    |     |     |     | 1170 |   |     |     |     |     |

| Arg | Ala | Leu | Gly | Glu | Arg | Pro | Val | Ala | Val | Asn |
|-----|-----|-----|-----|-----|-----|-----|-----|-----|-----|-----|
| CGC | GCG | CTC | GGC | GAA | CGC | CCG | GTC | GCG | GTG | AAC |
| 1185 |    |     |     |     | 1200 |   |     |     |     | 1215 |

FIGURE 5E

| Asp | Gly | Ser | Gly | Leu | Asp | Ala | Leu | Leu | Trp | Val |
|-----|-----|-----|-----|-----|-----|-----|-----|-----|-----|-----|
| GAC | GGC | TCC | GGC | CTG | GAC | GCG | CTC | CTG | TGG | GTC |
|     |     |     | 1230 |     |     |     |     |     | 1245 |     |

| Lys | Leu | Pro | Gly | Glu | Ser | Asp | Gly | Ala | Cys | Asn |
|-----|-----|-----|-----|-----|-----|-----|-----|-----|-----|-----|
| AAG | CTG | CCC | GGC | GAG | TCC | GAC | GGC | GCG | TGC | AAC |
|     |     |     | 1260 |     |     |     |     | 1275 |     |     |

| Gly | Gly | Pro | Ala | Ala | Gly | Gln | Trp | Trp | Gln | Glu |
|-----|-----|-----|-----|-----|-----|-----|-----|-----|-----|-----|
| GGC | GGC | CCG | GCC | GCC | GGC | CAG | TGG | TGG | CAG | GAG |
|     |     |     | 1290 |     |     |     |     | 1305 |     |     |

| Ile | Ala | Leu | Glu | Met | Ala | Arg | Asn | Ala | Arg | Trp |
|-----|-----|-----|-----|-----|-----|-----|-----|-----|-----|-----|
| ATC | GCC | CTG | GAG | ATG | GCG | CGC | AAC | GCC | AGG | TGG |
| 1320 |    |     |     |     |     | 1335 |    |     |     |     |

@@@
TGA
1350

```
             ———————————————————→   ←———————
    GCTGAGACCTCGCCCACGACGAGCCCGCGGACGGCGCACGTGCGTCCGCGGG
←————     1365            1380          1395
    CTCGTCCGTCCGGCCGCGGGCGCCCGGACGTCGGGGCGGCGGGGACAATGGG
        1410          1425            1440
    GCGGTGGCAGGGCAGACGACGGACCGCACCCGACGACGGACGCGCCGCGCTC
1455                    1484            1499
    GACGTGTGGCGCGCCGACCCCGCAGGCGTGCCGACCCCGGCGCGGCGGACCG
       1514           1529           1544          1559
    CGGTCCGGTTCACGCTCGAGGAGCTCGCCGACGTGGCCCCCGGCAACGCGGT
               1574                   1598         1608
    CGAGGTGCGCGTCCCGCCGGACGGCGGCCGTGCAGGCCGTGCAGGGCCCGCG
         1618         1628        1638        1648        1658
    GCACACCCGGG      3'
      1668
```

FIGURE 5F

CHARACTERIZATION AND STRUCTURE OF AN ENDODGLUCANASE GENE OF *CELLULOMONAS FIMI*

This is a continuation of U.S. application Ser. No. 07/902,460, filed Jun. 19, 1992, now abandoned, which is a continuation of application Ser. No. 07/630,396 filed Dec. 18, 1990, now abandoned, which is a continuation of U.S. application Ser. No. 06/894,326, filed Aug. 7, 1986, now abandoned.

FIELD OF THE INVENTION

This invention is directed to a molecular clone of a gene from the microorganism *Cellulomonas fimi* and to products derived therefrom. The DNA sequence of this gene encodes for the synthesis of an enzyme, endogluconase, which is useful for the efficient enzymatic conversion of cellulose to glucose.

BACKGROUND OF THE INVENTION

The efficient conversion of cellulose to a carbohydrate such as glucose which can be used as a starting material for other products, or for the production of food for humans, has been an object of intense research activity for many years.

The digestive systems of human beings and many animals cannot break down and absorb nutrient value from cellulose. Only ruminating animals such as cows, which have four stomachs, are capable of breaking down and digesting the complex and highly stable cellulose molecule. Cellulose, if it could be conveniently and economically reduced to a readily human digestible product, would open up a completely new food source for human beings.

At the present stage of the biological development of mankind, petroleum hydrocarbons are utilized as starting products for many materials used by humans, for example, polymers such as polyethylene and polystyrene, gasoline for automobiles, and man-made fibres for clothing. Unfortunately, petroleum is a depleting non-renewable resource. Coal can be used as a substitute, but it also is a non-renewable resource. Cellulose, which is the backbone of most flora and occurs naturally on a renewable basis, if it could be efficiently and economically broken down into manageable carbohydrate, could provide a renewable resource which conceivably could replace, at least in part, petroleum or coal as a basic starting block for mankind's needs.

The biological conversion of cellulose to glucose requires the activity of three types of enzymes. The insoluble substrate is attacked first by extracellular cellulases, of which there are two major types: the endo-1,4-β-glucanases (EC 3.2.1.4), or Eng; and the exo-1,4-β-glucanases (cellobiohydrolases, EC3.2.1.91), or exoglucanases (Exg) (Mandels, 1982; Gilbert and Tsao, 1983). The cellobiose resulting from the action of these enzymes is converted to glucose by β-1,4-glucosidases (EC3.2.1.21) or cellobiases (Mandels, 1982; Gilbert and Tsao, 1983). The cellobiases are usually intracellular, but some are extracellular (Mandels, 1982).

The inventors have been characterizing the cellulase system of the bacterium, *Cellulomonas fimi* (Gilkes et al., 1984 a,b; Langsford et al., 1984) by cloning the genes determining all of the components of the system. It is intended to use the cloned genes to characterize the components of the system through nt sequencing and prediction of aa sequences from the nt sequences. Cellulase systems tend to be very complex, and their components can prove difficult to purify by biochemical methods (Mandels, 1982; Gilbert and Tsao, 1983). Gene cloning can serve to identify components when other methods have failed (Gilkes et al., 1984 a,b). The product of a cloned cellulase gene can be produced in a cellulase-free background in an appropriate host microorganism (Whittle et al., 1982; Gilkes et al., 1984 a; Skipper et al., 1985). The individual enzymes then can be used to reconstitute the original cellulase system. Appropriate mixing experiments would help to elucidate the interactions of the components and to define their roles in the degradation of cellulose.

SUMMARY OF THE INVENTION

This invention is directed to cloned *C. fimi* DNA fragments expressing Eng activities, the characterization and structure of the cenA gene, and an analysis of functional regions of the protein.

The DNA sequence in *Cellulomonas fimi* which encodes an endo 1,4-β-glucanase EC3.2.1.4 (endoglucanase) has been cloned and determined. The total amino acid sequence of the endoglucanase has been determined from the DNA sequence, and a partial sequence confirming this has been determined directly by analysing the purified protein. The gene directs the synthesis of an enzyme which is necessary for the efficient enzymatic conversion of cellulose to glucose.

A derivative of the cloned gene on plasmid pcEC-2 in *Escherichia coli* C600 has been deposited at American Type Culture Collection, Rockville, Md., U.S.A., under ATCC No. 67101.

It is known that the enzymatic process developed for the conversion of cellulose to glucose will require endoglucanase as an essential component. Isolation of the gene and determination of its sequence thus facilitates development of such a process. The sequence of the gene can be manipulated to improve the characteristics of the enzyme, e.g., increasing the activity of the enzyme to increase the rate of conversion of cellulose to glucose, or by increasing the rate of production of the enzyme so that more cellulose can be degraded. Similarly, the stability of the enzyme to pH and temperature can be improved by altering the sequence of the gene.

In one aspect, the present invention is directed to a biologically pure plasmid having therein a DNA sequence with encodes an endo 1,4-β-glucanase (endoglucanase) which is useful for the efficient conversion of cellulose to glucose.

In another aspect, this invention is directed to an isolated cenA gene which is useful for synthesizing an endoglucanase enzyme which hydrolyses β-1,4 glycosidic linkages in the interior of a cellulose molecule.

DRAWINGS

DETAILED DESCRIPTION OF THE INVENTION

DEFINITIONS

Figure 1A:
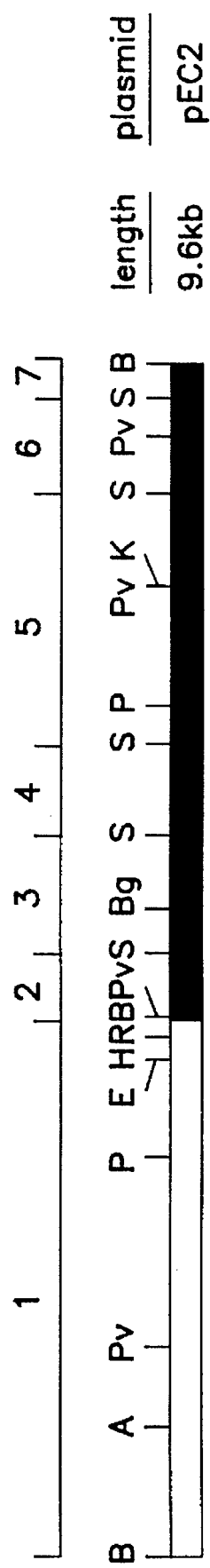
FIGS. 1a through 1d represents a diagram of plasmid pEC2 and its deletion derivatives pEC2.1, pEC2.2 and pEC2.3. The circular plasmids are shown in a linear fashion for clarity of comparison.

The following abbreviations and symbols are used in the specifications and claims.

| | |
|---|---|
| aa | amino acid(s) |
| Ap | ampicillin |
| BamHI | a prototypic restriction enzyme which recognizes the nucleotide sequence G GATCC |
| bp | base pair(s) |
| cDNA | complementary DNA |
| CMC | carboxymethylcellulose |
| CMCase | carboxymethylcellulase |
| cenA | gene coding for Eng |
| DNA | deoxyribonucleic acid |
| Eng | endoglucanase(s) |
| Exg | exoglucanase(s) |
| ExoIII | exonuclease III |
| Genome | entire complement of genetic material in a chromosome set |
| IPTG | isoporopyl- -D-thiogalactopyr-anoside |
| kb | 1000 bp |
| KDal | kilodalton(s) |
| $M_r$ | apparent relative molecular mass |
| mRNA | messenger RNA |
| nt | nucleotide(s) |
| ONPG | o-nitrophenyl- -D-galactoside |
| Palindrome | a sequence of DNA that is the same when opposite strands are read in the same direction (eg. 5' to 3') |
| Plasmid | autonomous self-replicating extra chromosomal circular DNA |
| PolIk | Klenow (large) fragment of E. coli DNA polymerase I |
| Promoter | region of DNA involved in binding of RNA polymerase to initiate transcription |
| R | resistant |
| Replication | DNA synthesis |
| Replicon | the unit which controls individual acts of replication; it has an origin at which replication is initiated and it may have a terminus at which replication stops |
| RF | replicative form |
| RNA | ribonucleic acid |
| rRNA | ribosomal RNA |
| S | sensitive |
| SDS | sodium dodecyl sulfate |
| Tc | tetracycline |
| Transcription | synthesis of RNA using a DNA template |
| Translation | synthesis of protein on a mRNA template |
| u | unit(s) |
| Vector | a plasmid or phage into which a foreign DNA may be inserted to be cloned |
| XGal | 5-bromo-4-chloro-3-indolyl-β-D-galactopyranoside |

The term "corresponds" in its various grammatical forms is used herein and in the claims in relation to nucleotide sequences to mean the nucleotide sequence described containing only conservative codon substitutions that encode for particular amino acid residues along the protein sequence.

The term "conservative codon substitution" as used above is meant to denote that one codon has been replaced by another leading to translation of a protein in which an amino acid residue has been replaced by another, biologically similar residue. Examples of conservative substitutions at the amino acid residue (translation) level include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, replacement of an ionic residue by another ionic residue of opposite charge is considered herein to be "radical replacement", as are replacements between non-ionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

At the nucleotide level, the term "corresponds" is also meant to denote that a nucleotide of a codon can be replaced by another nucleotide so that the codon containing the conservative substitution encodes for the same amino residue as did the unsubstituted codon. Such redundancy of different codons being translated to the same amino acid residue is well known in the art, as elsewhere discussed herein.

The term "biologically pure" as used herein refers to a biological substance free from all heterogeneous or extraneous matter.

When used in a context describing or depicting nucleotide sequences, the purine or pyrimidine bases forming the nucleotide sequences are depicted as follows:

A—deoxyadenyl

G—deoxyguanyl

C—deoxycytosyl

T—thymidyl

In describing a nucleotide sequence each three-letter triplet constituted by the bases identified above represents a trinucleotide of DNA (a codon) having a 5'-end on the left and a 3'-end on the right.

The amino acid sequences of the proteins described herein and defined by the claims are depicted by their three-letter or single-letter symbols that are identified and correlated in below:

| SYMBOLS FOR AMINO ACIDS | | |
|---|---|---|
| | Three-Letter | Single-Letter |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |

-continued

SYMBOLS FOR AMINO ACIDS

| | Three-Letter | Single-Letter |
|---|---|---|
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Full citations of the scientific publications referenced throughout the specification are provided in a References section herein below. Amino acid residues of proteins and polypeptides are in their natural, L, configurations.

GENERAL

Two BamHI fragments (0.8 and 5.2 kb) of *Cellulomonas fimi* containing an endoglucanase (Eng) gene (cenA) were individually cloned into the BamHI site of pBR322. They were found to express carboxymethylcellulase activity in *Escherichia coli*. The nucleotide (nt) sequence of the cenA gene was determined by sequencing overlapping deletions. The cenA gene has been found to be 1350 bp long encoding a polypeptide of 449 amino acids (aa) and a stop codon. The 0.8-kb BamHI component encodes the first 76 aa, whereas the 5.2-kb BamHI component encodes the rest of the Endoglucanase (Eng). The Eng lacking the N-terminal 76 aa retains its activity and antigenicity, and it forms an active fusion protein with the N-terminal portion of the Tc$^R$ determinant. The C-terminal region of the Eng is crucial for activity and deletion of as little as 12 aa from that end has been found to result in the loss of all Eng activity. The N-terminal 31 aa of the Eng constitute a leader peptide which appears to be functional in exporting the enzyme to the periplasm in *E. coli*.

MATERIALS USED AND GENERAL METHODS FOLLOWED (a) Bacterial Strains, Media and Vectors Except for *E. coli* JM101, the bacterial strains and the media used for their cultivation have been known and described previously (Whittle et al., 1982; Gilkes et al., 1984a). *E. coli* JM101 was the host for the M13 phage vectors (Messing, 1979; Yanisch-Perron et al., 1985). The plasmids pBR322 (Bolivar et al., 1977), pEC2 (Gilkes et al., 1984a) and phage M13mp18 (Yanisch-Perron et al., 1985) have been described previously.

(b) Enzyme Assays and Identification of Plasmid-coded Proteins

Cellulase activity in the total cell extracts prepared by the French press procedure (Whittle et al., 1982) was measured colorimetrically using CMC as substrate (Miller et al., 1960). One unit of enzyme released 1 umol of glucose equivalents per min, as determined by reference to a standard curve. Plasmid-encoded proteins were identified in maxicells (Sancar et al., 1979) after immunoprecipitation (Ivarie and Jones, 1979; Gilkes et al., 1984a).

(c) DNA Isolation and Fractionation

The isolation of chromosomal DNA from *C. Fimi* has been described previously (Whittle et al., 1982). Plasmid DNA for restriction analysis was isolated by the alkaline lysis procedure (Maniatis et al., 1982). Plasmid DNA to be sequenced was purified by banding in CsCl-ethidium bromide density gradients (Manjarls et al., 1982). The M13 RF and viral DNAs were isolated from infected cultures (Messing, 1983). DNA restriction fragments were resolved by agarose gel electrophoresis (Maniatis et al., 1982).

(d) Enzymes and Reagents

All restriction endonucleases were purchased from Bethesda Research Labs or PL Biochemicals; and were used as recommended by the suppliers. T4 DNA ligase, SI nuclease, ExoIII, PolIk, and T4 DNA polymerase were purchased from PL Biochemicals. Calf intestinal phosphatase was obtained from Boehringer-Mannheim. IPTG, Xgal and ONPG were obtained from Sigma. Nitrocefin was received from Glaxo Group Res. Ltd., Greenford, England. Radioactive deoxyribonucleoside 5'-triphosphates and $^{35}$S-methionine were obtained from NEN.

SPECIFIC PROCEDURES AND RESULTS OBTAINED (a) The Localization of the cenA Gene in pEC2

The original library of *C. fimi* genes was constructed by ligating a BamHI digest of genomic DNA into the BamHI site of pBR322. *E. coli* was transformed with the plasmid mixture. Ap$^R$, Tc$^S$ clones were screened for expression of *C. fimi* cellulases with antibody prepared against proteins secreted by *C. fimi* during growth on cellulose. Positive clones were characterized further by determination of enzymatic activities (Whittle et al., 1982; Gilkes et al., 1984a). The clone, pEC2, was shown to encode an Eng (Gilkes et al., 1984b) on an insert of about 5.2 kb (Gilkes et al., 1984a). The gene was localized within the insert by deleting portions of the insert using the restriction endonucleases AvaI and PvuII (see FIG. 1).

FIG. 1 represents a diagram of the plasmid pEC2 and its deletion derivatives pEC2, pEC2.1, pEC2.2 and pEC2.3. The circular plasmids are shown in a linear fashion for the clarity of comparison. (a) pEC2; (b) pEC2.1; (c) pEC2.2; and (d) pEC2.3. The open bar represents pBR322 DNA. The solid bar represents *C. fimi* DNA. The dashed lines represent the regions deleted in each derivative. The total length of each plasmid is indicated; the *C. fimi* inserts are 5.2 kb in (a); 1.9 kb in (b); 2.4 kb in (c); and, 3.5 kb in (d). The deletions in (b) and (d) extend to the AvaI site (A) and the PvuII site (Pv) of pBR322, respectively. However, the PvuII site was not regenerated in (d) after religation. The deletion in (c) was confined within the two SmaI or AvaI sites (S/A) of the insert. The numbers 1 to 7 represent the restriction fragments obtained by digesting (a) with BamHI+SmaI. Restriction enzymes are: A, AvaI; b, BamHI; Bg, BglII; E, EcoRI; H, HindIII; K, KpnI; p, PstI; Pv, PvuII; R, EcoRV; and S, SmaI.

Figure 1B:
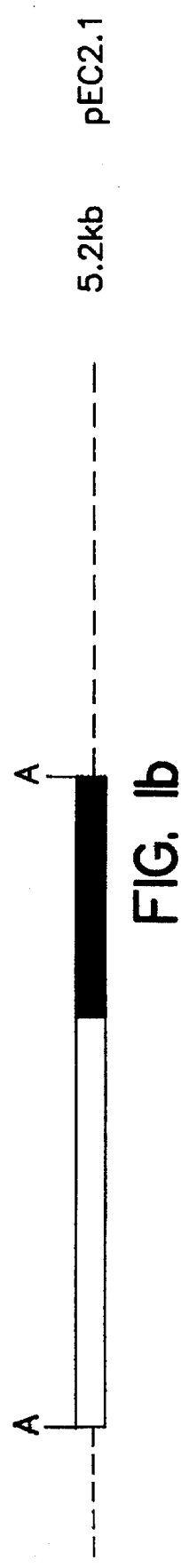
Figure 1C:

The shortest, uninterrupted fragment of the 5.2-kb insert which expressed CMCase activity equal to that of pEC2 was 1.4-kb long; it was found in pEC2.2 (see FIG. 1c; Table I below). Two other subclones expressed as much CMCase activity as pEC2. These were pEC2.1 and pEC2.3 (see FIGS. 1b and d; Table I below). All three clones shared the lefthand 1.4-kb fragment of the 5.2-kb insert. It was concluded that the Eng coding sequence was contained within this 1.4-kb fragment.

(b) The Eng Expressed as a Fusion Protein in *E. coli*

Figure 1D:
Figure 2:
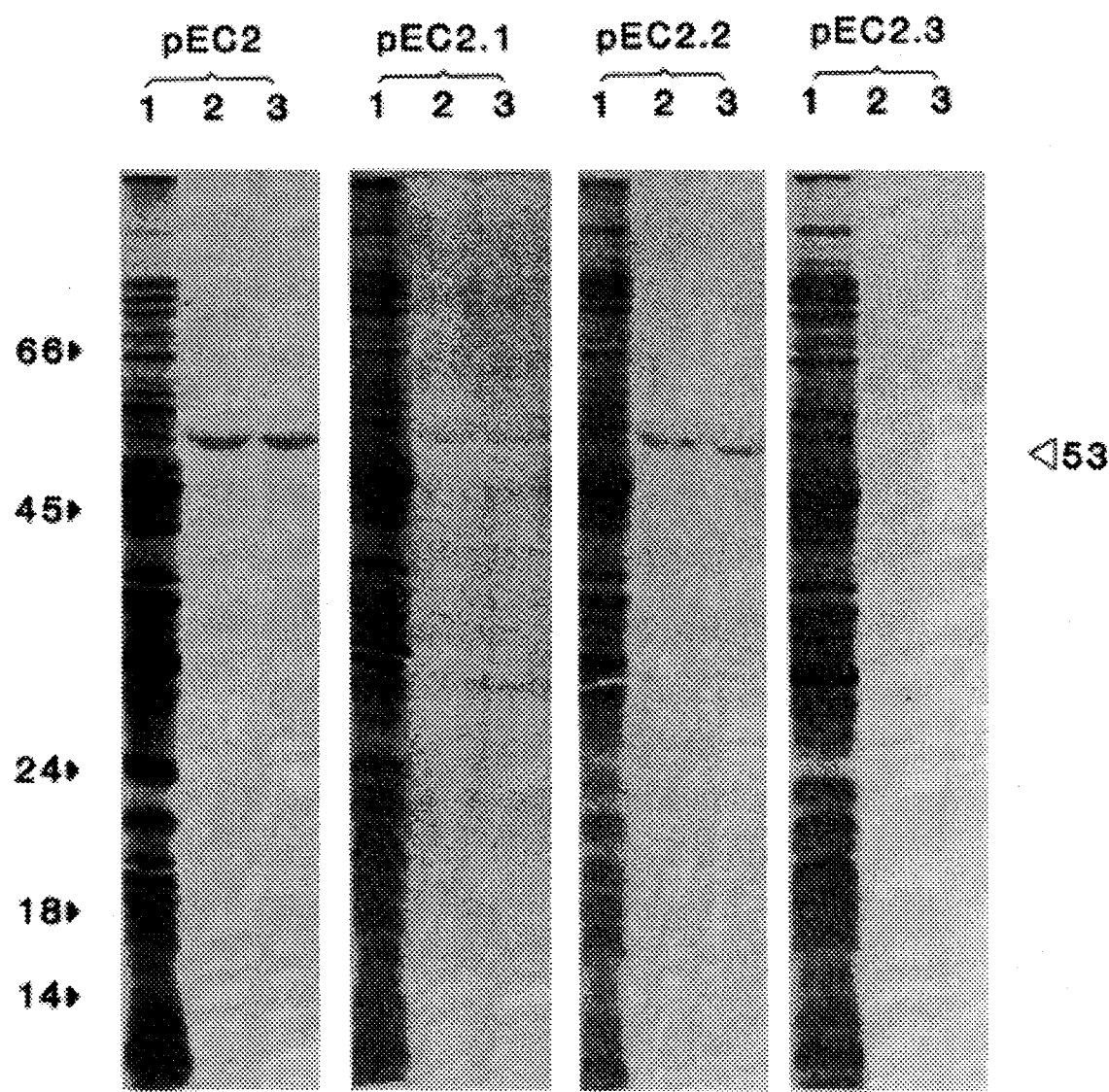
FIG. 2 depicts the immunoprecipitation of polypeptides encoded by pEC2 and its deletion derivatives, pEC2.1, pEC2.2 and pEC2.3.

All of the deletion mutants described in FIG. 1 were found to encode an immunoprecipitable polypeptide of 53 kDa (see FIG. 2).

FIG. 2 illustrates the immunoprecipitation of polypeptides encoded by pEC2 and its deletion derivatives. It was found that *E. coli* CSR603 was transformed with either pEC2, pEC2.1, pEC2.2, or pEC2.3. The proteins encoded by each plasmid were labelled according to the maxicell procedures of Sancar et al. (1979). The labelled proteins were then precipitated with antibodies against the Eng, and the precipitates were analysed by SDS-polyacrylamide gel electrophoresis as described previously (Gilkes et al., 1984a). Four sets of protein samples are shown, and each set is derived from one of the four plasmids as indicated. Lanes 1, the labelled proteins before treatment with antisera; lanes 2, the protein precipitated with a monoclonal antibody A2/23.11.32 (Langsford et al., 1984) directed against *C. fimi* cellulase; lanes 3, protein precipitated with antisera raised against CMC-induced *C. fimi* extracellular enzymes (Whittle et al., 1982). The open triangle indicates the immunoprecipitated protein in lanes 2 and lanes 3 of all four samples. Close triangles represent $M_r$ markers; and numbers refer to sizes (kDa).

Since all of the deletion mutants described in FIG. 1 encoded an immuno-precipitable polypeptide of 53 kDa (FIG. 2), it was concluded that the sequence encoding CMCase activity and antigenicity lies within the 1.4-kb fragment of *C. fimi* DNA common to the four plasmids. However, a fragment of 1.4 kb is not quite sufficient to encode a 53-kDa polypeptide. This suggested that the CMCase activity determined by the plasmids was a fusion polypeptide containing a fragment of the $Tc^R$ determinant and the Eng. In this case, the cenA gene would lack the *C. fimi* transcriptional and translational signals controlling the expression of the gene and a portion of the N-terminal coding sequence. This was supported by the fact that either inverting the *C. fimi* insert with respect to the $Tc^R$ promoter (Stuber and Bujard, 1981) or deleting the $Tc^R$ promoter resulted in a drastic reduction of cellulase expression from the respective constructs (see Table I; pEC2.2i, pEC2.1 HB). In addition, frameshift mutations introduced into the $Tc^R$ coding portion of the proposed fusion protein led to a loss of CMCase activity (see Table I; pEC2.1 Ks, pEC2.1 RB).

(c) Cloning of the N-Terminus of the cenA Gene

In order to clone the N-terminus of the cenA gene, a partial BamHI digest of *C. fimi* DNA was ligated into the BamHI site of pBR322. Clones were screened by the CMC plate assay (Teather and Wood, 1982). The plasmids from CMCase-producing clones were digested to completion with BamHI. A plasmid, pcEC2, was obtained that contained the 5.2-kb fragment of pEC2 (FIG. 1a) and an additional 0.8-kb fragment 5' to the region known to code for CMCase activity. The 0.8-kb and 5.2-kb fragments were shown to be contiguous on the *C. fimi* genome by Southern hybridization analysis (see FIG. 3).

Figure 3A:
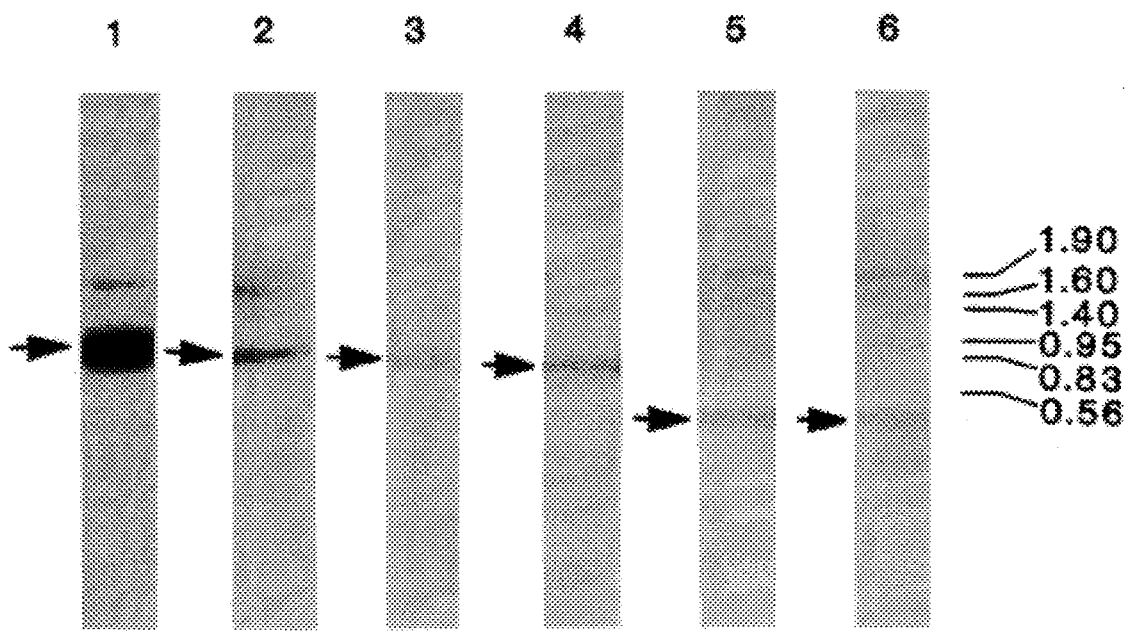
FIG. 3(a) represents the hybridization results of the DNA's restricted with an AvaII probe.
Figure 3B:
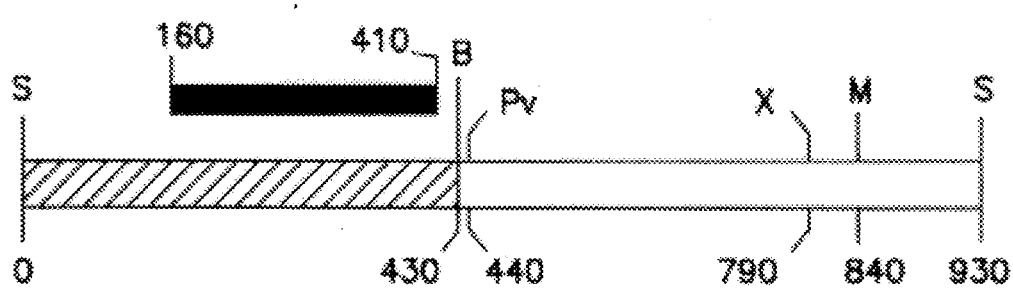
FIG. 3(b) represents a restriction map of a SmaI fragment derived from pcEC2.

FIG. 3 represents evidence that the 0.8-kb fragment and the *C. fimi* insert of pEC2 are contiguous on the *C. fimi* genome. *C. fimi* genomic DNA was cleaved to completion by SmaI. The DNA was then digested with either MluI, XhoI, PvuII, or BamHI. The cleaved DNAs were fractionated by 1.2% agarose gel electrophoresis, and hybridized with a $^{32}$P-labelled AvaII probe according to the procedures of Southern (1975). The AvaII probe was obtained from the 0.8-kb fragment (as shown in b), and was labelled with [$-^{32}$p]dATP,—dGTP, and —dCTP by PolIk. FIG. 3(a) depicts the hybridization results of the restricted DNAs with the AvaII probe. Lane 1: pcEC2 digested with SmaI (positive control). Lane 2–6: *C. fimi* DNA digested with SmaI (lane 2), SmaI+MluI (3), SmaI+XhoI (4), SmaI+PvuII (5), and with SmaI+BamHi (6). The arrows indicate the hybridized bands that would be expected from the restriction map of pcEC2. The numbers indicate the positions of the smaller size markers (in kb) of DNA digested with EcoRI+HinIII. FIG. 3(b) presents a restriction map of the SmaI fragment derived from pcEC2. The hatched bar represents the 0.8-kb portion; the open bar represents the portion from pEC2's insert; the solid bar represents the AvaII probe. The numbers are the coordinates in bp. Restriction enzymes are: B, BamHI; M, MluI; Pv, PvuII; S, SmaI; and X, XhoI.

The 0.8-kb BamHI fragment from pcEC2 was purified and ligated into BamHI-digested pEC2.1 (FIG. 1b). When the fragment was inserted in the same orientation as in pcEC2, this plasmid, designated pcEC2.1, gave the same level of CMCase activity as pcEC2 (Table I). However, when the fragment was inserted in the opposite orientation, this plasmid, designated pciEC2.1, gave very little CMCase activity (Table I below). This suggested first that the 0.8-kb fragment contained a translation initiation signal and second that the entire Eng-coding sequence lay within the 2.2 kb comprising the 0.8-kb fragment and the first 1.4 kb of the 5.2-kb fragment of *C. fimi* DNA.

(d) The Sequence of the cenA Gene

The BamHI fragment in pEC2.2 (FIG. 1c) was 2.4-kb long, and it contained the 1.4 kb to the right of the junction. The fragment was subcloned into M13mp18, and a series of unidirectional, overlapping deletions was generated in it with ExoIII (Henikoof, 1984; see legend to FIG. 5 below). This approach allowed the sequencing of the left-hand part of the fragment preferentially, because the time of digestion with ExoIII could be adjusted to give a series of deletions of approximately the required length.

A novel procedure was used to generate deletions for use in sequencing the 0.8-kb BamHI fragment from pcEC2. The procedure allowed the isolation in a simple screening of a set of six overlapping sequences, three for each complementary strand, which covered the entire fragment (see FIG. 4).

Figure 4A:
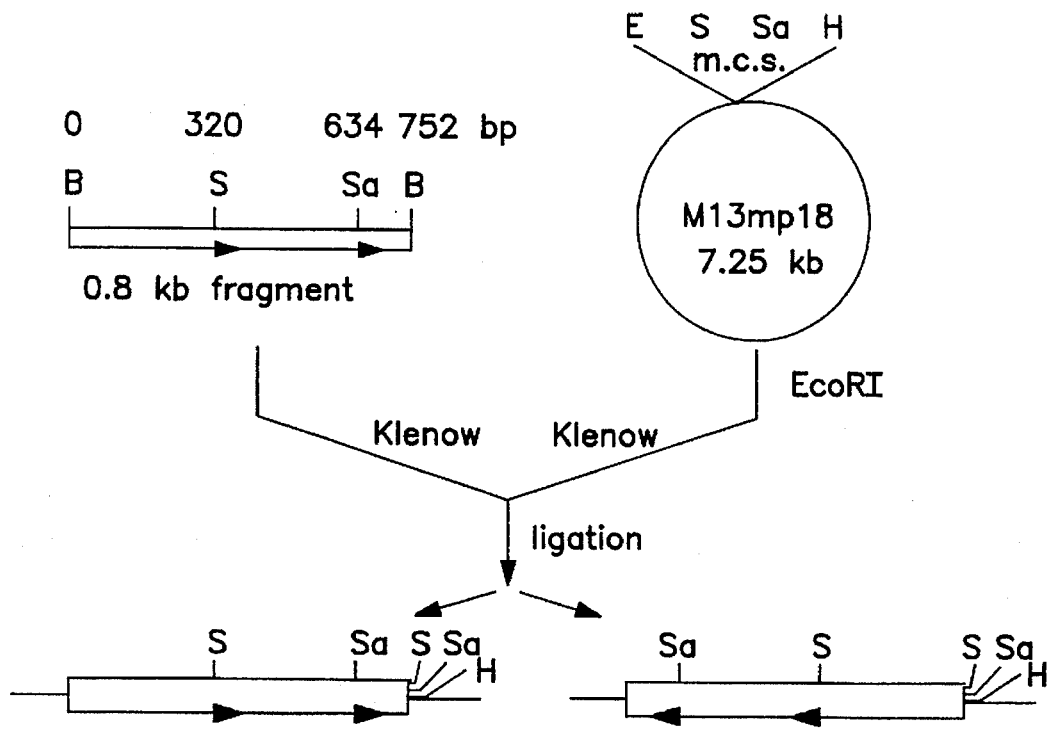
FIGS. 4a through 4c represents a sequence flow-chart of the protocol used for producing and screening deletions; and, FIGS. 5A through 5F represents the nucleotide sequence of the nucleic acid (the cenA gene) and the amino acid sequence of the Endoglucanase protein, deduced from the gene.
Figure 4B:
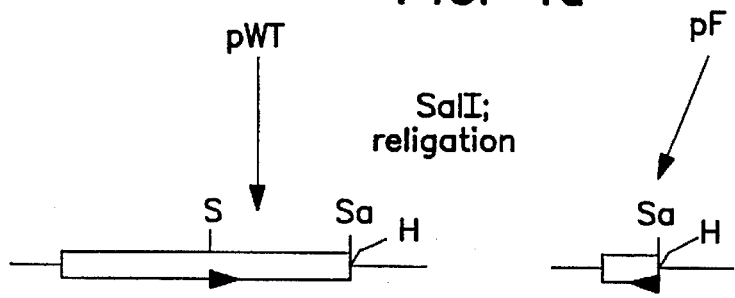
Figure 4C:
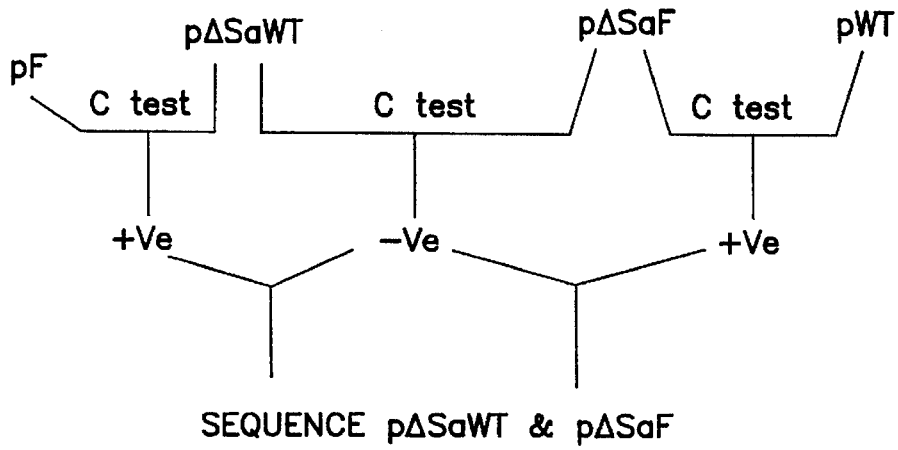

FIG. 4 represents a flowsheet of the protocol for production and screening of deletions. Specifically, the following protocol was used for producing and screening deletions created by SalI cleavage of the 0.8-kb fragment from pcEC2. (A) The 0.8-kb BamHI fragment (open bar; arrows indicate direction of transcription) was cloned into the EcoRI site of M13mp18 (m.c.s. represents the multiple-cloning sites). Two recombinant DNA products, pWT and pF, carried the 0.8-kb fragment in opposite orientations; they were screened by restriction analysis of RF molecules. (B) The RF DNA from each phage type was cleaved with SalI, diluted, and religated. (C) The deletion mutants were identified by a rapid phage hybridization test (C test; Messing, 1983). Each unknown phage of the class p SaWT was annealed with an unknown phage of the class p SaF. Those which did not anneal were then annealed with pF and pWT, respectively. Those which annealed were sequenced (see FIG. 5). The same procedure was used to generate SmaI (S) deletions for sequencing. Restriction enzymes are: B, BamHI; E. EcoRI; H, HindIII; S. SmaI; and Sa, SalI.

The sequence corresponding to the cenA gene was located and its reading frame was established by matching the aa sequences predicted by the nt sequence with the sequence of the first 31 aa at the N-terminus of the Eng purified from *C. fimi* (FIG. 5). The nt sequence determining these 31 aa falls entirely within the 0.8-kb fragment of pcEC2. A putative start codon (ATG) occurs 93 nt upstream from the first nt of the codon defining the N-terminal alanine of the mature Eng. The first stop codon in frame with this ATG is a TGA 1347 nt downstream from the A of ATG. This means that the primary translation product of the cenA gene is 449 aa long, and that the first 31 aa at the N-terminus are removed to generate the mature Eng of 418 aa. The predicted aa composition of the mature enzyme agrees closely with that determined for the enzyme purified from *C. fimi*. The predicted sequence gives a protein with an $M_r$ of 51,837. The enzyme as purified from *E. coli* has an apparent $M_r$ of 51,837. The enzyme as purified from *C. fimi* has an apparent $m^R$ of 58,000; however, this form of the enzyme is glycosylated (Gilkes et al., 1984; Langsford et al., 1984).

(e) Transcriptional and Translational Signals for the cenA Gene

FIG. 5 illustrates the nt sequence of the cenA gene and the deduced aa sequence of the Eng protein. The strategy of generating unidirectional overlapping deletions of the 2.4-kb BamHI insert of pEC2.2 is essentially the same as described (Henikoff, 1984) except for the following changes. The BamHI insert was blunt ended with PolIk and was ligated in both orientations with EcoRI cleaved M13mp18 (sticky ends filled in by PolIk). 5 ug of the recombinant RF DNA (of each orientation) were used as the starting material. The DNA was cleaved completely with BamHI to give an ExoIII susceptible end and with PstI to produce an ExoIII resistant end. The conditions used for the ExoIII treatment were as described previously except that 12 aliquots of treated DNA were removed successively at intervals of 30 min. The ExoIII reaction was stopped, and aliquots of DNA were treated successively with S1 nuclease, PolIk and DNA ligase. 20 ul of each ligated sample was used to transfect *E. coli* JM101 cells by standard procedures (Messing, 1983). RF DNA was prepared from individual plaques (Messing, 1983) and analyzed using restriction endonucleases. Clones containing DNA of appropriate insert size were chosen for the sequencing. Sequencing of the overlapping deletion fragments from the two BamHI fragments was performed by the dideoxy termination method (Sanger et al., 1977). The coding region (set in triplets) starts at +1 (A of ATG) and ends at +1347. the last digit of each number is aligned with the numbered nt. A Shine-Dalgarno (S. D.) type sequence before the ATG start codon is underlined. The downward arrow indicates the leader sequence processing site. The underlined aa residues were determined by automated Edman degradation of the purified native Eng. The BamHI site between the 0.8-kb fragment and the insert of pEC2 is boxed. A prominent (pro-thr)$_4$-thr-(pro-thr)$_7$ aa sequence is overlined.

As can be seen in FIG. 5, the TGA stop codon is followed closely by a perfect 16-bp palindrome which could be a transcriptional termination signal. The 16-bp palindromic sequence following the stop codon is indicated by the inverted arrows. The sequence preceding the ATG start codon contains a potential ribosome-binding site (Shine and Dalgarno, 1974; FIG. 5), but it does not contain a sequence resembling other prokaryotic promoter sequences (Moran et al., 1982; Hawley and McClure, 1983). However, S1 mapping indicated a potential transcriptional start point 46 nt upstream from the start codon. The expression of the gene in *E. coli* depends on the Tc$^R$ promoter. When the Tc$^R$ promoter (Stuber and Bujard, 1981) was removed from pcEC2.1, the level of expression of the cenA gene was reduced by 94% (Table I, pcEC2.1 HB). This suggests that the presumed promoter from *C. fimi* was not functional in *E. coli*.

(f) Functional Regions of the Eng

The expression of the cenA gene fragment in pEC2 and its derivatives as an active fusion polypeptide shows that the N-terminal fragment of the native enzyme is not essential for the enzyme activity. It remains to be determined if its absence affects the kinetics or substrate binding of the enzyme. It is possible that the N-terminus of the Tc$^R$ determinant substitutes to a degree for the missing segment of the enzyme.

Deletion of DNA coding for the last 12 aa from the C-terminal end of the cenA gene (FIG. 5) by ExoIII digestion resulted in the loss of all Eng activity (data not shown). This demonstrates that the C-terminus of the Eng is essential for activity. However, it is not yet clear if these aa are directly or indirectly involved in active site function.

(g) The Signal Peptide of the Eng

The nt sequence of the cenA gene predicts an initial sequence of 31 aa having many of the features of protein signal sequences such as charged aa at the N-terminus, lengthy hydrophobic sequence, and a gln-ala-ala processing site (Inouye and Halegoua, 1980; Kreil, 1981; Watson, 1984; Wickner and Lodish, 1985). This sequence appears to function in the export of the Eng to the periplasm in *E. coli*. More than 50% of the CMCase activity determined by pcEC2 is found in the periplasm (Table II below). This contrasts with the cellular location of the polypeptide determined by pEC2. The Eng leader sequence is missing in this plasmid, and only 15% of the CMCase activity it determines is found in the periplasm (Table II). This latter "Eng" is a hybrid protein, with the N-terminus of the Tc$^R$ determinant of pBR322 replacing the first 76 aa of the pre-Eng. The Tc$^R$ determinant is an integral membrane protein (Sutcliffe, 1979; Nguyen et al., 1983), which implies that its N-terminus has features which lead to the incorporation of the Tc$^R$ protein into the membrane (Kreil, 1981; Nguyen et al., 1983; Wickner and Lodish, 1985). However, the Tc$^R$ N-terminus does not operate as efficiently for secretion of the Eng as does the signal peptide of the Eng itself.

(h) The pro-thr Sequence of the Eng

The predicted aa sequence of the mature Eng contains a very striking feature. The aa 143–165 corresponding to nucleotides 426–495, respectively are either threonine or proline (see FIG. 5). The sequence of these residues corresponds very closely with a sequence containing only proline and threonine which occurs in the predicted aa sequence of an Exg from *C. fimi* (O'Neill et al., 1986). The function of this conserved sequence remains to be determined.

TABLE I

This Table tabulates the Eng activities of various cenA clones

| Clone | Description | CMCase specific activity[a] | Ref. |
|---|---|---|---|
| pEC2 | parental clone | 0.215[b] | FIG. 1a |
| PEC2.1 | Eng$^+$ deletion | 0.279 | FIG. 1b |
| pEC2.2 | derivatives of pEC2 | 0.259 | FIG. 1c |
| pEC2.3 | | 0.232 | FIG. 1d |
| pEC2.2i | derivatives of pEC2 produced to investigate transcription | 0.00077 | c |
| pEC2.1 HB | | 0.00056 | d |
| pEC2.1Ks | derivatives of pEC2 produced to investigate translation | 0.0059 | e |
| pEC2.1 RB | | 0.0056 | f |

TABLE I-continued

This Table tabulates the Eng activities of various cenA clones

| Clone | Description | CMCase specific activity[a] | Ref. |
|---|---|---|---|
| pcEC2 | pEc2 plasmid with the 0.8-kb fragment at the insert's 5' end | 0.0152 | RESULTS AND DISCUSSION Section c |
| pcEc2.1 | products of functional investigation of the 0.8-kb fragment | 0.0150 | RESULTS AND DISCUSSION Section c |
| pciEC2.1 | | 0.00047 | |
| pcEC2.1 HB | derivative of pcEC2.1 with the Tc[R] promoter deleted | 0.00090 | g |

LEGEND
[a]Specific activity is expressed as U/mg of protein, where U is umol of glucose equivalents released per min.
[b]From Gilkes et al. (1984 a,b).
[c]Obtained by inverting the BamHI insert of pEC2.2.
[d]Obtained by deleting the small HindIII-BamHI fragment containing the Tc[R] promoter (Stuber and Bujard, 1981) from pEC2.1.)
[e]Obtained by linearizing pEC2.1 with BamHI, filing in the cohesive ends with PolIK, and ligating the resulting blunt ends.
[f]Obtained by deleting the smaller EcoRV-BamHI fragment from pEC2.1.
[g]Obtained by deleting the smaller HindIII-BamHI fragment from pcEC2.1.

TABLE II

This Table tabulates the distribution of enzyme activities in different cellular locations of clones pEC2 and pcEC2

| Activity | Clone | Total extract | Cytoplasmic fraction | Periplasmic fraction |
|---|---|---|---|---|
| CMCase[c] | pEC2 | 0.063 (0.215) | 0.063 (0.167) | 0.00949 (0.529) |
| | pcEC2 | 0.00472 (0.0152) | 0.00222 (0.006) | 0.00264 (0.148) |
| B-lactamase[d] | pEC2 | 815.93 (2550) | 47.18 (125.2) | 700 (39002) |
| | pcEC2 | 911.7 (2348) | 53.45 (117.3) | 745 (35975) |
| B-galactosidase[e] | pEC2 | 0.923 (2.88) | 1.11 (2.95) | 0.00571 (0.32) |
| | pcEC2 | 0.941 (2.42) | 1.13 (2.48) | 0.00663 (0.32) |

Enzyme activity[a] (and specific activity[b])

LEGEND
[a]Proteins from total cell extracts were prepared by breaking the cells using a French press (Whittle et al., 1982). Periplasmic proteins were isolated by osmotic shock (Nossal and Heppel, 1966). Cytoplasmic proteins were prepared by rupturing the osmotically-shocked cells with a French press. The unbracketed numbers represent the respective activity (U of enzyme/ml of cell culture) of CMCase, B-lactamase and B-galactosidase of pEC2 and pcEC2 clones.
[b]The numbers in parentheses represent the repective specific activity (U of enzyme/mg of protein) of CMCase, B-lactamase and B-galactosidase of pEC2 and pcEC2 clones.
[c]CMCase activity was assayed as described in MATERIALS AND METHODS, section b; U for CMCase activity is umol of glucose equivalents released per min.
[d]B-lactamase activity was determined with nitrocefin as described by O'Callaghan et al. (1972); U for B-lactamase activity is umol of nitrophenol acid produced per min.
[e]B-galactosidase activity was measured with ONPG as the substrate (Miller, 1972); U for B-galactosidase activity is umol of o-nitrophenol produced per min.

REFERENCES

Bolivar, F., Rodriguez, R. L., Greene, P. J., Betlach, M. V., Heynecker, H. L., Boyer, H. W., Crosa, J. H., and Falkow, S.: Construction and characterization of new cloning vehicles, II. A multipurpose cloning system. Gene 2 (1977) 95–113.

Gilbert, I. G. and Tsao, G. T.: Interaction between solid substrate and cellulase enzymes in cellulose hydrolysis. Ann. Rept. Ferm. Proc. 6 (1983) 323–358.

Gilkes, N. R., Kilburn, D. G., Langsford, M. L., Miller Jr., R. C., Wakarchuk, W. W., Warren, R. A. J., Whittle, D. J. and Wong, W. K. R.: Isolation and characterization of Escherichia coli clones expressing cellulase genes from Cellulomonas fimi. J. Gen. Microbiol. 130 (1984a) 1377–1384.

Gilkes, N. R., Langsford, J. L., Kilburn, D. G., Miller Jr., R. C., and Warren R. A. J.: Mode of action and substrate specificities of cellulases from cloned bacterial genes. J. Biol. Chem. 259 (1984b) 10455–10459.

Hawley, D. K. and McClure, W. R.: Compilation and analysis of Escherichia coli promoter DNA sequences. Nucl. Acids Res. 11 (1983) 2237–2255.

Henikoff, S.: Unidirectional digestion with exonuclease III creates targeted breakpoints for DNA sequencing. Gene 28 (1984) 351–359.

Inouye, M. and Halegoua, S.: Secretion and membrane localization of proteins in Escherichia coli. CRC crit. Rev. Biochem. 7 (1980) 339–371.

Ivarie, R. D. and Jones, P. O.: A rapid, sensitive assay for specific protein synthesis in cells and cell-free translation: use of Staphylococcus aureus as an adsorbant for immune complexes. Anal. Biochem. 97 (1979) 24–35.

Kreil, G.: Transfer of proteins across membranes. Ann. Rev. Biochem. 50 (1981) 317–348.

Langsford, M. L., Gilkes, N. R., Wakarchuk, W. W., Kilburn, D. G., Miller Jr., R. C. and Warren, R. A. J.: The cellulase system of Cellulomonas fimi. J. Gen. Microbiol. 130 (1984) 1367–1376.

Mandels, M.: Cellulases. Ann. Rept. Ferm. Proc. 5 (1982) 35–78.

Maniatis, T., Fritsch, E. F. and Sambrook, J.: Molecular Cloning: a Laboratory Manual. Cold Spring Harbor Laboratory, Cold Spring Harbor, N.Y. 1982.

Messing, J.: A multipurpose cloning system based on the single-stranded DNA bacteriophage M13. Recombinant DNA Technical Bulletin, NIH publication No. 79–99, Vol. 2, No. 2 (1979) 43–48.

Messing, J.: New M13 vectors for cloning. Methods Enzymol. 101 (1983) 20–79.

Miller, G. L., Blum, R., Glennon, W. E. and Burton, A. L.: Measurement of carboxymethylcellulase activity. Anal. Biochem. 2 (1960) 127–132.

Miller, J. H.: Experiments in Molecular Genetics. Cold Spring Harbor Laboratory, Cold Spring Harbor, N.Y., 1972.

Moran, C. P. Jr., Lang, N., LeGrice, S. F. J., Lee, G., Stephens, M., Sonenshein, A. L., Pero, J. and Losick, R.: Nucleotide sequences that signal the initiation of transcription and translation in *Bacillus subtills*. Mol. Gen. Genet. 186 (1982) 339–346.

Nguyen, T. T., Postle, K. and Bertrand, K. P.: Sequence homology between the tetracycline-resistance determinants of Tn10 and pBR322: Gene 25 (1983) 83–92.

Nossal, N. G. and Heppel, L. A.: The release of enzyme by osmotic shock from *Escherichia coli* in exponential phase J. Biol. Chem. 241 (1966) 3055–3062.

O'Callaghan, C. J., Morris, A., Kirby, S. M. and Shingler, A. H.: Novel method for detection of B-lactamase by using a chromogenic cephalosporin substrate. Antimicrob. Ag. Chemother. 1 (1972) 283–288.

Sancar, A., Hack, A. and Rupp, W. D.: A simple method for identification of plasmid coded proteins. J. Bacteriol. 137 (1979) 692–693.

Sanger, F., Nicklen, S. and Coulson, A. R.: DNA sequencing with chain terminating inhibitors. Proc. Natl. Acad. Sci. USA 74 (1977) 5463–5467.

Shine, J. and Dalgarno, L.: The 3'-terminal sequence of *Escherichia coli* 16S ribosomal RNA: complementary to nonsense triplets and ribosome binding sites. Proc, Natl. Acad. Sci. USA 72 (1974) 1342–1346.

Skipper, N., Sutherland, M., Davies, R. W., Kilburn, D., Miller Jr, R. C. Warren, A. and Wong, R.: Secretion of a bacterial cellulase by yeast. Science 230 (1985) 958–960.

Southern, E. M.: Detection of specific sequences among DNA fragments separated by gel electrophoresis. J. Mol. Biol. 98 (1975) 503–517.

Stuber, D. and Bujard, H.: Organization of transcriptional signals in plasmids pBR322 and pACYC184. Proc. Natl. Acad. Sci. USA 78 (1981) 167–171.

Sutcliffe, J. G.: Complete nucleotide sequence of the *Escherichia coli* plasmid pBR322. Cold Spring Harbor Symp. Quant. Biol. 43 (1979) 77–90.

Teather, R. M. and Wood, P. J.: Use of Congo red-polysaccharide interactions in enumeration and characterization of celluloytic bacteria from bovine rumen. Appln. Environ. Microbiol. 43 (1982) 777–780.

Watson, M. E. E.: Compilation of published signal sequences. Nucl. Acids Res. 12 (1984) 5145–5164.

Wichner, W. T. and Lodish, H. F.: Multiple mechanisms of protein insertion into and across membranes. Science 230 (1985) 400–407.

Whittle, D. J., Kilburn, D. G., Warren, R. A. J. and Miller Jr, R. C.: Molecular cloning of a *Cellulomonas fimi* cellulase gene in *Escherichia coli*. Gene 17 (1982) 139–154.

Yanisch-Perron, C., Vieira, J. and Messing, J.: Improved M13 phage cloning vectors and host strains: nucleotide sequences of the M13mp18 and pUC19 vectors. Gene 33 (1985) 103–119.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. An isolated DNA comprising nucleotides 526 to 1673 numbered from the 5' terminus of the coding region as represented in FIG. 5.

2. An isolated DNA comprising nucleotides 1 to 1347 numbered from the 5' terminus of the coding region as represented in FIG. 5.

3. An isolated DNA comprising nucleotides 94 to 1347 numbered from the 5' terminus of the coding region as represented in FIG. 5.

4. An isolated microorganism host having a plasmid that comprises an origin of replication and a DNA comprising nucleotides selected from the group consisting of: nucleotides 526 to 1673, nucleotides 1 to 1347, nucleotides 94 to 1347, and nucleotides 94 to 1673 numbered from the 5' terminus of the coding region as represented in FIG. 5.

5. The isolated microorganism host of claim 4, wherein raid microorganism host is a bacterium.

6. The host of claim 5 wherein the bacterium is a strain of *Escherichia coli*.

7. A culture of the microorganism *Escherichia coli* C600 having the characteristics of ATCC No. 67101.

8. A plasmid comprising (1) a 0.8 kilobase BamHI fragment from pcEC2 contiguous with and operatively linked to (2) a 5.2 kilobase BamHI fragment of *Cellulomonas fimi* DNA wherein said (1) and (2) encode an endoglucanase enzyme which hydrolyzes beta-1,4-glycosidic linkages in a cellulose molecule.

9. The plasmid of claim 8, wherein the apparent relative molecular mass of said endoglucanase enzyme is about 51 to 58 kilodaltons.

10. The plasmid of claim 8, wherein said endoglucanase enzyme is glycosylated when expressed in *Cellulomas fimi*.

11. A plasmid selected from the group consisting of pEC2.1, pEC2.2 and pcEC2.

12. A plasmid comprising vector DNA and a DNA comprising a *Cellulomas fimi* CenA gene or a portion thereof encoding a polypeptide with endoglucanase activity, with the proviso that said DNA includes at least a portion of the 0.8 kilobase BamH1 fragment of pcEC2.

13. The plasmid according to claim 12, wherein said vector DNA is pBR322.

14. An isolated DNA comprising a *Cellulomas fimi* CenA gene or a portion thereof encoding a polypeptide with endoglucanase activity, with the proviso that said DNA includes at least a portion of the 0.8 kilobase BamH1 fragment from pcEC2.

15. The DNA according to claim 14, wherein a portion of said DNA is selected from the group consisting of:

(a) the DNA represented in FIG. 5;

(b) the SmaI fragment of pcEC2;

(c) the first 1.4 kb of a 5.2 kb BamHI fragment of *Cellulomonas fimi* DNA; and (d) a 2.2 kb DNA comprising the 0.8 kb fragment from pcEC2 and the first 1.4 kb of the 5.2 kb BamHI fragment of *Cellulomonas fimi* DNA.

16. An *E. coli* host cell containing a plasmid comprising vector DNA and DNA comprising a *Cellulomonas fimi* cenA gene or a portion thereof encoding a polypeptide with endoglucanase activity, with the proviso that said DNA is other than a 5.2 kb BamHI fragment of *Cellulomonas fimi* DNA.

17. An isolated DNA comprising the coding region of the *Cellulomonas fimi* cenA gene as shown in FIG. 5.

18. An isolated DNA comprising: a sufficient portion of a *Cellulomonas fimi* CenA gene which when expressed provides a polypeptide having endoglucanase activity, said DNA including at least a portion of an 0.8 kilobase BamH1 fragment from pcEC2, and up to the entire coding region of the *Cellulomonas fimi* CenA gene as represented in FIG. 5.

19. A biologically pure plasmid comprising the DNA according to claim 17.

20. A microorganism host containing a plasmid according to claim 19.

21. A DNA comprising nucleotides selected from the group consisting of: nucleotides 526 to 1673, nucleotides 1 to 1347, 94 nucleotides to 1347, and nucleotides 94 to 1673 numbered from the 5' terminus of the coding region as represented in FIG. 5.

22. A recombinant DNA comprising as operably linked components a transcriptional promoter and a DNA comprising nucleotides selected from the group consisting of: nucleotides 526 to 1673, nucleotides 1 to 1347, nucleotides 94 to 1347, and nucleotides 94 to 1673 numbered from the 5' terminus of the coding region as represented in FIG. 5.

23. A recombinant DNA according to claim 22, further comprising a translation initiating codon and translation terminating codon operably linked to said second-mentioned DNA.

24. An isolated DNA which encodes a polypeptide having endoglucanase activity and which is exported to the periplasm of *E. coli*, wherein said DNA comprises all or a portion of the CenA gene represented in FIG. 5.

25. A biologically pure plasmid comprising vector DNA and a DNA comprising nucleotides selected from the group consisting of: nucleotides 526 to 1673, nucleotides 1 to 1347, nucleotides 94 to 1347, and nucleotides 94 to 1673 numbered from the 5' terminus of the coding region as represented in FIG. 5.

26. A biologically pure plasmid comprising vector DNA and a transcriptional promoter operably linked to a DNA comprising a *Cellulomonas fimi* CenA gene or a portion thereof encoding a polypeptide with endoglucanase activity wherein sid DNA is selected from the group consisting of: nucleotides 526 to 1673, nucleotides 1 to 1347, and nucleotides 94 to 1347 numbered from the 5' terminus of the coding region as represented in FIG. 5.

27. An *E. coli* host cell containing a plasmid comprising vector DNA and a transcriptional promoter operably linked to a DNA comprising a *Cellulomonas fimi* cenA gene or a portion thereof encoding a polypeptide with endoglucanase activity, wherein said DNA is selected from the group consisting of: nucleotides 526 to 1673, nucleotides 1 to 1347, and 94 to 1347 numbered from the 5' terminus of the coding region as represented in FIG. 5.

28. The host cell according to claim 27, wherein said plasmid further comprises a translation initiating codon and translation terminating codon operably linked to said DNA.

* * * * *